United States Patent
Hadjicostis et al.

(10) Patent No.: US 7,628,785 B2
(45) Date of Patent: Dec. 8, 2009

(54) ENDOSCOPIC MEDICAL TREATMENT INVOLVING ACOUSTIC ABLATION

(75) Inventors: Andreas Hadjicostis, Carmel, IN (US); Jared Brosch, Cicero, IN (US); Michael H. Phillips, Indianapolis, IN (US)

(73) Assignee: Piezo Technologies, Indianapolis, IN (US)

( * ) Notice: Subject to any disclaimer, the term of this patent is extended or adjusted under 35 U.S.C. 154(b) by 950 days.

(21) Appl. No.: 10/868,415

(22) Filed: Jun. 14, 2004

(65) Prior Publication Data

US 2004/0254570 A1 Dec. 16, 2004

Related U.S. Application Data

(60) Provisional application No. 60/478,649, filed on Jun. 13, 2003.

(51) Int. Cl.
*A61B 18/04* (2006.01)
*A61B 8/14* (2006.01)

(52) U.S. Cl. .......................... 606/27; 600/471
(58) Field of Classification Search ............... 606/27, 606/28, 41; 600/439, 459, 471; 601/2, 3
See application file for complete search history.

(56) References Cited

U.S. PATENT DOCUMENTS

| | | | |
|---|---|---|---|
| 4,669,467 A | 6/1987 | Willett et al. | |
| 4,998,527 A | 3/1991 | Meyer | |
| 5,304,173 A | 4/1994 | Kittrell et al. | |
| 5,409,483 A * | 4/1995 | Campbell et al. | 606/15 |
| 5,471,988 A | 12/1995 | Fujio et al. | |
| 5,492,126 A | 2/1996 | Hennige et al. | |
| 5,588,432 A * | 12/1996 | Crowley | 600/439 |
| 5,630,837 A * | 5/1997 | Crowley | 601/2 |
| 5,693,043 A | 12/1997 | Kittrell et al. | |
| 5,906,580 A | 5/1999 | Kline-Schoder et al. | |
| 5,938,612 A | 8/1999 | Kline-Schoder et al. | |
| 6,004,269 A | 12/1999 | Crowley et al. | |
| 6,235,024 B1 | 5/2001 | Tu | |
| 6,315,776 B1 | 11/2001 | Edwards et al. | |
| 6,321,109 B2 | 11/2001 | Ben-Haim et al. | |
| 6,383,151 B1 * | 5/2002 | Diederich et al. | 601/2 |
| 6,405,732 B1 | 6/2002 | Edwards et al. | |
| 6,451,009 B1 | 9/2002 | Dasilva et al. | |
| 6,514,249 B1 | 2/2003 | Maguire et al. | |
| 6,547,788 B1 * | 4/2003 | Maguire et al. | 606/41 |
| 6,605,084 B2 * | 8/2003 | Acker et al. | 606/28 |
| 2004/0176757 A1 * | 9/2004 | Sinelnikov et al. | 606/27 |

FOREIGN PATENT DOCUMENTS

WO WO 02/39915 A1 5/2002

* cited by examiner

*Primary Examiner*—Michael Peffley
(74) *Attorney, Agent, or Firm*—Woodard, Emhardt, Moriarty, McNett & Henry LLP (57) ABSTRACT

In one embodiment, an endoscope has a proximal end portion opposite a distal end portion. A view port is included at the distal end portion to view an internal body region through a passageway of a patient's body. Also located at the distal end portion are one or more piezoelectric elements operable in one mode to determine position of the distal end portion relative to internal body region and operable in a second mode to ablate tissue of the internal body region. The endoscope carries a balloon positioned about the one or more piezoelectric elements to selectively hold the distal end portion in a desired position in the passageway.

7 Claims, 10 Drawing Sheets

ENDOSCOPIC MEDICAL TREATMENT INVOLVING ACOUSTIC ABLATION

CROSS-REFERENCE TO RELATED APPLICATIONS

The present application claims the benefit of U.S. Provisional Patent Application No. 60/478,649 filed 13 Jun. 2003, which is hereby incorporated by reference. The present application is related to the commonly owned U.S. patent application Ser. No. 10/686,310 filed 15 Oct. 2003; Ser. No. 10/686,120 filed 15 Oct. 2003; and Ser. No. 10/686,119 filed 15 Oct. 2003, all of which are hereby incorporated by reference.

BACKGROUND

The present invention relates to acoustic ablation techniques, and more particularly, but not exclusively, relates to endoscopic medical treatment apparatus, devices, systems, and methods involving acoustic ablation—particularly for treatment of the esophagus.

The ability to selectively remove tissue from a portion of the human body with a minimal degree of trauma has led to the development of various therapeutic procedures. Indeed, minimally invasive techniques have been developed that involve accessing a treatment site through a body passageway, such as the vasculature, the gastrointestinal tract, and the like. One particular area of interest is the removal of tissue from the esophagus to treat a pre-cancerous condition, known as "Barrett's Esophagus." It is believed that this condition affects millions of people. International Patent Application Publication Number WO 02/39915 A1 describes various schemes to remove tissue associated with Barrett's Esophagus.

Frequently, these and other approaches do not provide a desired degree of control over various parameters associated with the targeting of ablation energy on the tissue. Thus, there is an ongoing demand for further contributions in this area of technology. Moreover, advances in this area of technology can have application in medical treatments other than the esophagus and/or in nonmedical procedures.

SUMMARY

One embodiment of the present invention is a unique acoustic ablation technique. Other embodiments include unique methods, systems, devices, and apparatus for generating acoustic energy. As used herein, "ultrasound" and "ultrasonic" refer to acoustic energy waveforms having a frequency of more than 20,000 Hertz (Hz) through one or more media at standard temperature and pressure.

A further embodiment includes an endoscope with a distal end portion carrying a selectively inflatable balloon and one or more piezoelectric elements inside the balloon. In one form, the one or more piezoelectric elements number substantially more than two, and different groups of the elements are selectively activated to corresponding ablate different tissue regions. Alternatively or additionally, the one or more elements are utilized in one mode for imaging and another mode to perform tissue ablation.

Still a further embodiment is directed to a medical treatment device that includes a distal end portion opposite a proximal end portion. The proximal end portion connects to operator equipment outside a patient's body. The distal end portion extends through a passageway of the patient's body to an internal body region. The device further includes a balloon to selectively hold the distal end portion in the passageway, an optical port at the distal end portion to visualize the internal body region, and an acoustic ablation array positioned inside the balloon that includes several piezoelectric elements position about a central axis of the distal end portion.

Yet a further embodiment includes an endoscope with a proximal end portion opposite a distal end portion that is operable to extend the distal end portion through a passageway of a patient's body and dispose it in a selected position proximate to an internal body region. The distal end portion includes: an optical port for visualizing the internal body region, a balloon operable to maintain the position of the distal end portion proximate to the internal body region when inflated, and an acoustic ablation array positioned inside the balloon that includes several piezoelectric elements. Also included is operator equipment positioned outside the patient's body that is coupled to the proximal end portion of the endoscope. This equipment includes: a device to display one or more images of the internal body region through the optical port, a balloon control port in fluid communication with an interior of the balloon to selectively expand the balloon by providing fluid under pressure thereto, and a signal controller operable to activate one or more elements of the array to selectively ablate tissue while the distal end portion is held in the position within the patient's body.

Another embodiment includes: disposing a distal end portion of a medical treatment device inside a passageway of a patient's body proximate to an internal region while leaving a proximal end portion of the medical treatment device outside the patient's body, viewing one or more images of the internal region through an image communication pathway extending between the distal end portion and the proximal end portion, expanding a balloon carried on the distal end portion with an acoustic ablation array carried inside the balloon at the distal end that has several piezoelectric elements, and activating different groups of the elements while the position of the distal end portion is maintained by balloon expansion to correspondingly provide ultrasonic energy focused to ablate tissue of the internal region circumferentially surrounding the distal end portion.

Still another embodiment, includes: disposing a distal end portion of a medical treatment device inside a passageway of a patient's body proximate to an internal body region, viewing one or more images of the internal body region from an image communication pathway extending between the distal end portion and the proximal end portion, activating one or more piezoelectric elements in an imaging mode to determine location of the one or more elements relative to the internal body region with the one or more elements being located at the distal end portion inside a balloon, expanding the balloon to maintain position of the distal end portion proximate to the internal body region, and ablating tissue of the internal body region by activating the one or more piezoelectric elements in an ablation mode.

Yet another embodiment includes an endoscope with a proximal end portion opposite a distal end portion. The endoscope includes: means for positioning the distal end portion proximate to an internal body region through a passageway of a patient's body, means for viewing the internal body region through a port positioned proximate to the internal body region, means for imaging the internal body region with one or more piezoelectric elements positioned at the distal end portion, means for ablating tissue of the internal body region with the one or more piezoelectric elements, and means for selectively holding the distal end portion in position in the passageway proximate to the internal body region that includes a balloon positioned about the one or more piezoelectric elements.

One object of the present invention is to provide a unique ultrasonic ablation technique.

Another object of the present invention is to provide a unique method, system, device, or apparatus for generating acoustic energy.

Further forms, objects, features, aspects, benefits, advantages, and embodiments of the present invention shall become apparent from the detailed description and drawings provided herewith.

DETAILED DESCRIPTION OF SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

One embodiment of the present invention is an acoustic ablation device including a distal end portion and a proximal end portion, with the distal end portion being inserted into the patient's body and carrying an expandable balloon and one or more piezoelectric elements to ablate tissue or determine the location of the distal end portion. The balloon is expanded to hold the distal end portion in a selected position. The proximal end portion is connected to operator equipment outside the patient's body. The distal end portion further includes a way to visualize/locate the internal body region.

Figure 1:
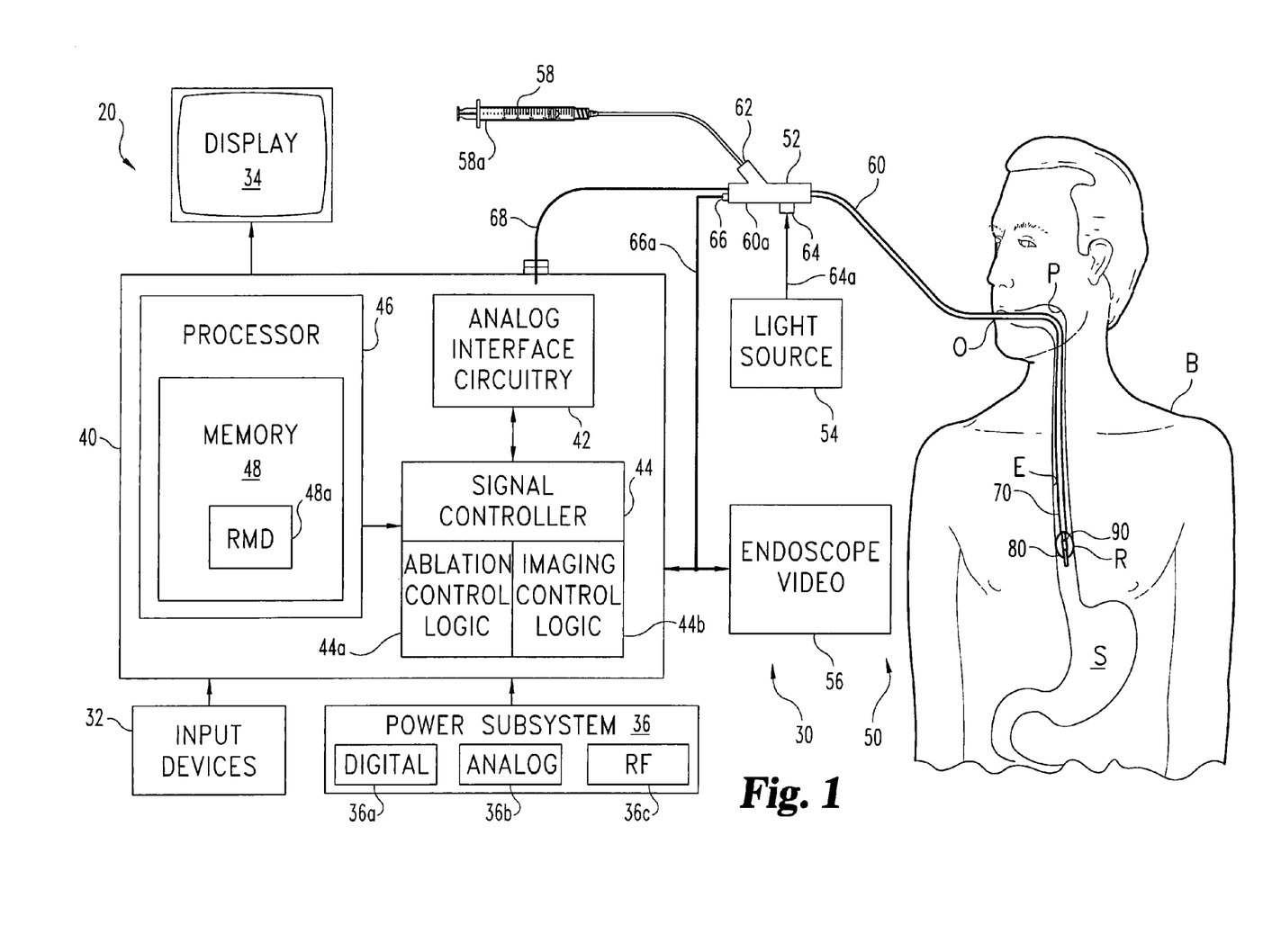
FIG. 1 is a schematic view of a system to provide medical treatment with a first type of transducer device.

FIG. 1 illustrates system 20 that includes an endoscopically disposed ultrasonic transducer array and associated equipment arranged to provide medical treatment. System 20 includes operator equipment 30. Operator equipment 30 includes operator input devices 32, operator display device 34, and various other operator-utilized equipment of system 20 that is external to body B of a patient during use. System 20 also includes subsystem 40 operably connected with operator input devices 32 and operator display device 34. Input devices 32 include an alphanumeric keyboard and mouse or other pointing device of a standard variety. Alternatively or additionally, one or more other input devices can be utilized, such as a voice input subsystem or a different type as would occur to those skilled in the art. Operator display device 34 can be of a Cathode Ray Tube (CRT) type, Liquid Crystal Display (LCD) type, plasma type, Organic Light Emitting Diode (OLED) type, or such different type as would occur to those skilled in the art. Alternatively or additionally, one or more other operator output devices can be utilized, such as a printer, video recorder, mass data storage device, one or more loudspeakers, headphones, or such different type as would occur to those skilled in the art. Operator equipment 30 also can include one or more communication interfaces suitable for connection to a computer network, such as a Local Area Network (LAN), Municipal Area Network (MAN), and/or Wide Area Network (WAN) like the internet; a medical diagnostic device; another therapeutic device; a medical imaging device; a Personal Digital Assistant (PDA) device; a digital still image or video camera; and/or audio device, to name only a few. Operator equipment 30 can be arranged to show other information under control of the operator.

Processing subsystem 40 processes signals and data associated with system 20. Subsystem 40 includes analog interface circuitry 42, signal controller 44, data processor 46, and memory 48. Analog interface circuitry 42 is responsive to control signals from signal controller 44 to provide corresponding analog stimulus signals via circuitry 42. Signal controller 44 includes ablation control logic 44a and imaging control logic 44b. At least one of analog circuitry 42 and signal controller 44 includes one or more digital-to-analog converters (DAC) to facilitate operation of system 20 in the manner to be described in greater detail hereinafter. Processor 46 is coupled to signal controller 44 to bidirectionally communicate therewith, to selectively provide output to display device 34, and to selectively respond to input from operator input devices 32.

Signal controller 44 and/or processor 46 can be of a programmable type; a dedicated, hardwired state machine; or a combination of these. Signal controller 44 and processor 46 perform in accordance with operating logic that can be defined by software programming instructions, firmware, dedicated hardware, a combination of these, or in a different manner as would occur to those skilled in the art. For a programmable form of signal controller 44 or processor 46, at least a portion of this operating logic can be defined by instructions stored in memory 48. Programming of signal controller 44 and/or processor 46 can be of a standard, static type; an adaptive type provided by neural networking, expert-assisted learning, fuzzy logic, or the like; or a combination of these.

Memory 48 is illustrated in association with processor 46; however, memory 48 can be separate from or at least partially included in one or more of signal controller 44 and processor 46. Memory 48 includes at least one Removable Memory Device (RMD) 48a. Memory 48 can be of a solid-state variety, electromagnetic variety, optical variety, or a combination of these forms. Furthermore, memory 48 and can be volatile, nonvolatile, or a mixture of these types. Memory 48 can be at least partially integrated with circuitry 42, signal controller 44, and/or processor 46. RMD 48a can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, RMD 48a is absent.

Circuitry 42, signal controller 44, and processor 46 can be comprised of one or more components of any type suitable to operate as described herein. Further, it should be appreciated that all or any portion of circuitry 42, signal controller 44, and processor 46 can be integrated together in a common device, and/or provided as multiple processing units. For a multiple processing unit form of signal controller 44 or processor 46; distributed, pipelined, and/or parallel processing can be utilized as appropriate. In one embodiment, circuitry 42 is provided as one or more components coupled to a dedicated integrated circuit form of signal controller 44; processor 46 is provided in the form of one or more general purpose central processing units that interface with signal controller 44 over a standard bus connection; and memory 48 includes dedicated memory circuitry integrated within signal controller 44 and processor 46, and one or more external memory components including a removable disk form of RMD 48a.

System 20 further includes power supply subsystem 36. As shown on FIG. 1, subsystem 36 includes digital device power supply 36a, analog device power supply 36b, and Radio Frequency (RF) power supply 36c. While subsystem 36 is shown with three separate supplies, it should be understood that one or more of these supplies can be configured together as an integral unit and/or one or more additional power supplies can be included as one or more separate units. Circuitry 42, signal controller 44, and/or processor 46 can include one or more signal filters, limiters, oscillators, format converters (such as DACs or digital-to-analog converters), or other signal operators, conditioners, components, and/or elements as appropriate to operate system 20 in the manner to be described in greater detail hereinafter.

System 20 also includes endoscope subsystem 50 operatively coupled to processing subsystem 40. Endoscope subsystem 50 includes endoscope 52 with light source 54 and endoscope video display device 56. Endoscope 52 includes proximal end portion 60 opposite distal end portion 70. At proximal end portion 60, endoscope 52 includes operator handle 60a, light port 64 which is coupled to light source 54 by light cable 64a, balloon control port 62 which is coupled to balloon control device 58, and image communication port 66 which is coupled to endoscope video device 56. Endoscope video device 56 is operably connected to processing subsystem 40 by video cable 66a. Typically, device 56 includes video recording and display apparatus, as well as standard controls to assist the operator. Control cable 68 extends from endoscope 52 to processing subsystem 40, to connect endoscope 52 with processing subsystem 40. Distal end portion 70 and proximal end portion 60 are connected by elongate, flexible body 72. Distal end portion 70 is introduced into and removed from body B through opening O, formed by the patient's mouth. Endoscope 52 includes components/controls to navigate distal end portion 70 through passageway P of body B in a standard manner, which may include various curves and turns to reach a desired location. In the illustration of FIG. 1, passageway P includes esophagus E of body B, which is shown relative to stomach S. Accordingly, through opening O and passageway P, a target internal body region R of esophageal tissue can be reached for diagnosis and/or therapeutic treatment. Distal end portion 70 includes balloon 80 that can be selectively expanded to maintain position once the target internal body region R of esophagus E is reached. Ballon 80 surrounds transducer 90 carried at the distal end portion 70, further aspects of which are described with reference to FIGS. 2 and 3.

Figure 2:
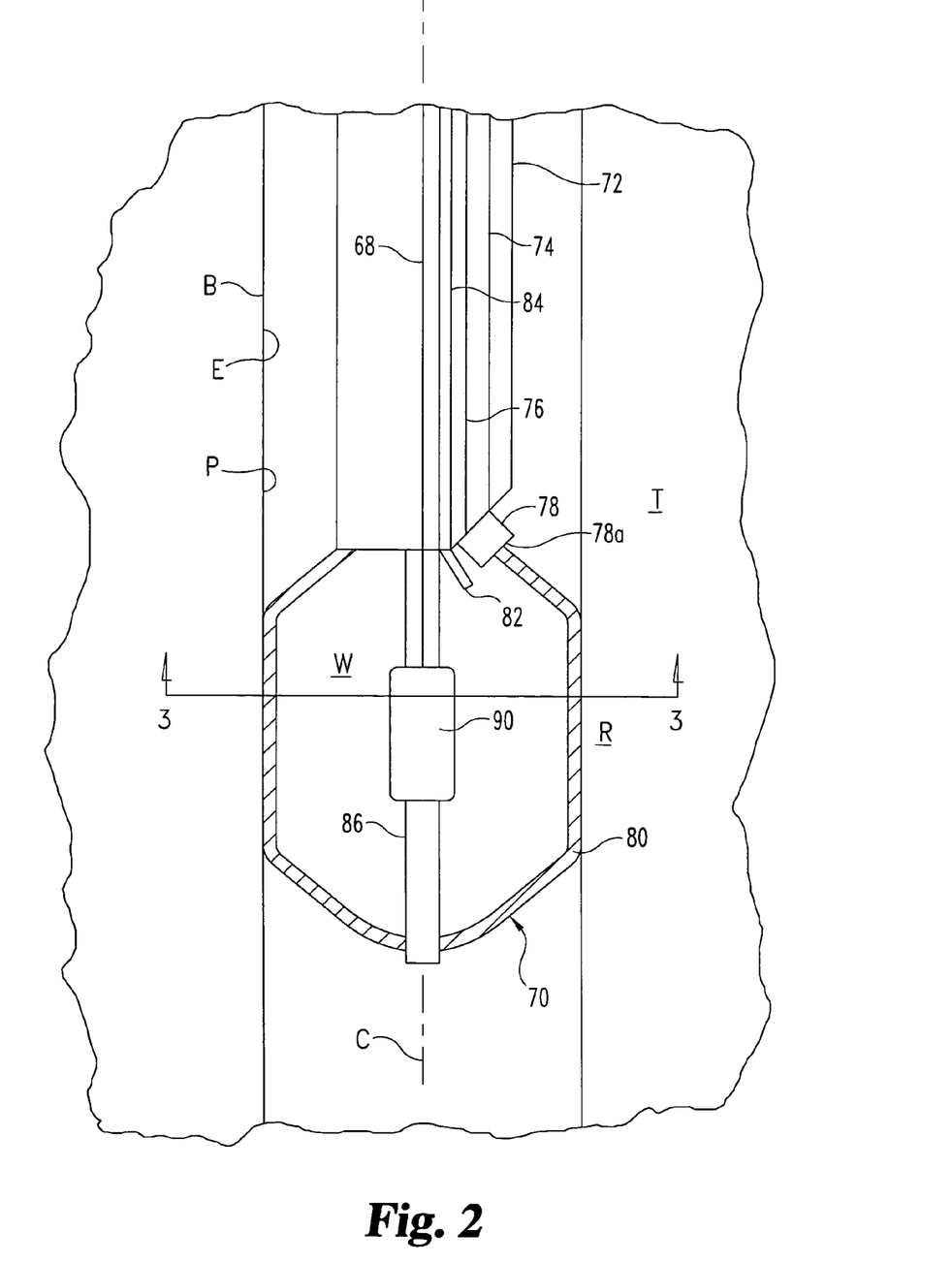
FIG. 2 is a partial sectional, schematic view of a distal end portion shown in FIG. 1.
Figure 3:
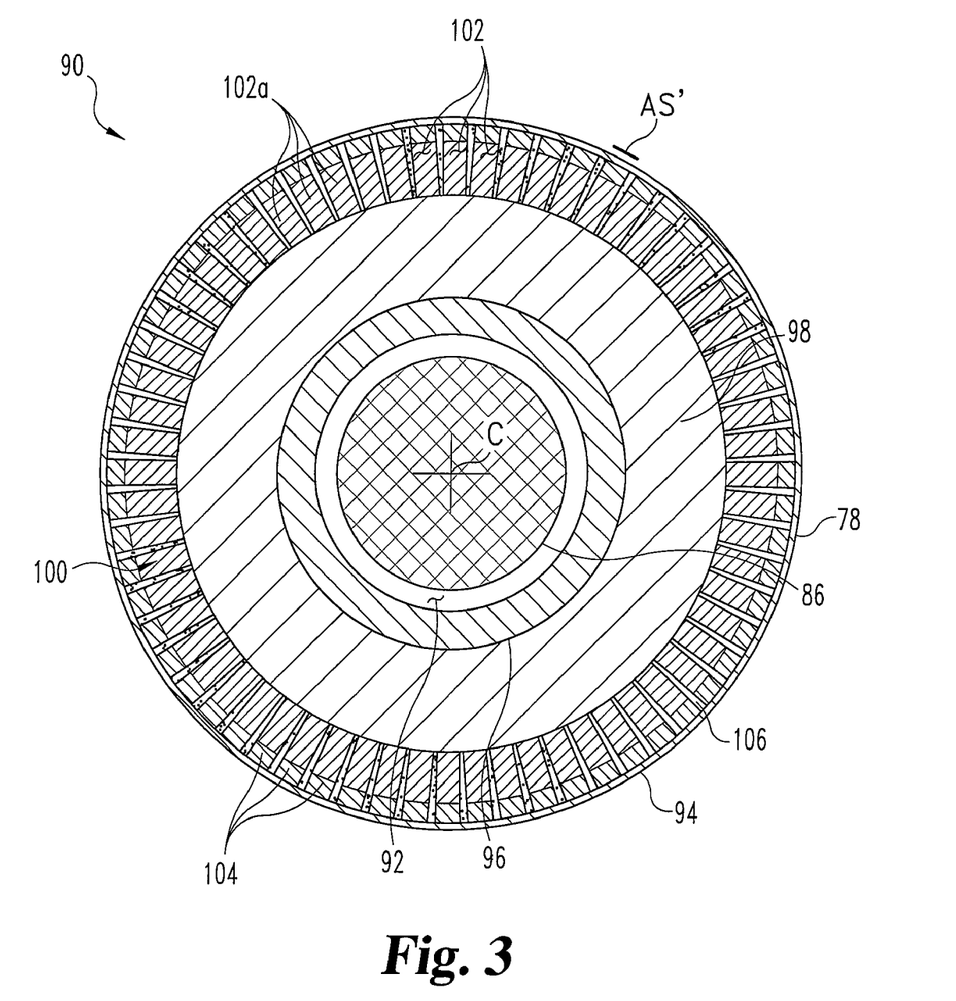
FIG. 3 is a sectional view of an ablation device taken along section line 3-3 shown in FIG. 2.

Referring to FIG. 2, a partial schematic, sectional view of distal end portion 70 is shown. FIG. 3 shows a cross-section of transducer 90 taken along section line 3-3 of FIG. 2. As can best be seen in FIG. 2, body 72 extends along longitudinal center axis C and encloses transducer control cable 68, light pathway 74, image communication pathway 76, and balloon fluid conduit 84. Image communication pathway 76 extends to video camera 78 which includes view port 78a. Additionally, light pathway 74 and/or image communication pathway 76 can include an optic fiber. Video camera 78 is oriented to visualize an adjacent wall region of passageway P with a view line perpendicular to axis C. Video camera 78 is located at the distal end of flexible body 72, and preferably includes a Charge Coupled Device (CCD) sensor matrix. The orientation of camera 78 is arranged to view tissue T of an esophagus E and determine the relation of distal end portion 70 to the internal body region R. It should be appreciated that video camera 78 can be oriented differently and/or located in a different position. Additionally, it should be understood that system 20 can operate in ablation mode and location determination mode without the presence of video camera 78. Distal end portion 70 includes balloon 80 which is in fluid communication with balloon fluid port 82, and surrounds transducer device 90 and supporting core 86. The balloon 80 expands when a fluid, such as a liquid or a gas, is introduced into the balloon 80 through the balloon fluid port 82. The balloon 80 expands to a point where it is in contact with esophagus E.

Referring to FIG. 3, transducer 90 includes flexible substrate 94 that carries ablation array 100. Flexible substrate 94 and ablation array 100 are shaped generally in the form of a right circular cylinder in FIG. 3. Ablation array 100 includes a number of piezoelectric elements 102 positioned in the interior of flexible substrate 94 of transducer device 90. Elements 102 are each made of a piezoelectric material that responds to an appropriate electrical stimulus to generate acoustic energy in the ultrasonic frequency range. Accordingly, elements 102 are designated ultrasonic transducers 102a. Elements 102 are each generally rigid relative to flexible substrate 94 and are elongate with a longitude generally parallel to center axis C. The longitudinal dimension of each elongate element 102 (extending generally parallel to center axis C) may alternatively be referred to as its length. The width of each elongate element 102 defines an arc segment AS' on the circumference of the device. Ablation array 100 therefore comprises a multiplicity of elongate elements 102 having individual widths that are less than the circumference of the device. Elements 102 are each generally sized and shaped the same, and are evenly spaced apart from one another.

In FIG. 3, center axis C is generally perpendicular to the view plane and is accordingly represented by cross-hairs that intersect at the origin of the circular cross section of transducer device 90. Correspondingly, center axis C is centrally located relative to array 100 in FIG. 3. Piezoelectric elements 102 are generally equidistant from center axis C, being spaced approximately evenly thereabout. In a preferred embodiment of the present application, elements 102 number 24 or more. In a more preferred embodiment, elements 102 number 64 or more. In an even more preferred embodiment, elements 102 number at least 256. Elements 102 can each be made of the same piezoelectric material. Alternatively, one or more elements 102 can be made of material different than one or more other of elements 102. Piezoelectric elements 102 are connected to metallic electrically conducting contacts 104 carried on substrate 94. In one form, connection between elements 102 and contacts 104 is made with an epoxy that does not unacceptably impede electrical contact. Elements 102 are interior to contacts 104 and are in contact with acoustic layer 98.

Transducer device 90 includes a support matrix material 106 between adjacent elements 102. Acoustic layer 98 is positioned between elements 102 and acoustic layer 96. Acoustic layer 96 is in contact with cylindrical backing member 92. Member 92 surrounds supporting core 86. In one embodiment, material 106 is a standard epoxy and acoustic layers 98 and 96 are formed from a thermoplastic and/or thermoset polymeric resin, such as parylene C polymer, selected to minimize transmission of ultrasonic energy from array 100 towards core 86. In another embodiment, the same composition is used for both material 106 and acoustic layers 98 and 96. In still other embodiments, one or more other materials or backing structures and/or support matrix materials 106 are used as would occur to those skilled in the art. In other embodiments, acoustic layers 98 and 96 are formed from metals such as aluminum, silicon, or tungsten, for example; or are absent, with the corresponding space being filled by air.

Referring generally to FIGS. 1-3, one mode of operating system 20 is next described. During normal use, distal end portion 70 of endoscope 52 is inserted through opening O of body B and advanced through passageway P. Distal end portion 70 is navigated into esophagus E to the desired internal body region R of esophagus E utilizing images conveyed through port 78a to operate equipment 30 via image communication pathway 76. These images may be displayed with display device 34 and/or video device 56 (if equipped with a display). Light to facilitate visualization in this way is provided from light source 54 that is coupled to port 78 via light pathway 74.

Thereafter, the balloon control device 58, which is in the form of syringe 58a, is coupled to port 62, and is operated to distribute liquid under pressure through balloon control port 62 into fluid conduit 84. The liquid from conduit 84 enters balloon 80 through fluid port 82, and expands the balloon 80 to hold the balloon in a selected position along passageway P adjacent region R. To verify proper positioning, system 20 can be operated in a mode to determine the location of transducer 90 relative to region R. In one form, this mode of operation is performed by activating each of elements 102 separately to ascertain whether transducer 90 is "centered' within esophagus E. In one mode of operation, transducer 90 generates an ultrasonic signal of 20 Mhz or less that is reflected back to and detected by transducer 90. The reflected signal is processed by subsystem 40 to determine the distance from transducer 90 to the interface of balloon 80 and tissue T. This locating information is used to direct high intensity focused ultrasound (HIFU) energy to the desired region R. In one particular mode, this operating mode can be used to generate an ultrasonic image to assist with positioning. This relative position determination can be performed before, during, and after balloon expansion, as desired. Further, this mode can be executed before and after a tissue ablation mode of operation of transducer 90, which is described in detail next.

After positioning, array 100 of transducer device 60 is controllably activated with operator equipment 30 to selectively ablate tissue T in region R by application of acoustic power from one or more of elements 102 in the ultrasonic range through the balloon 80 and the fluid inside balloon 80.

Figure 4:
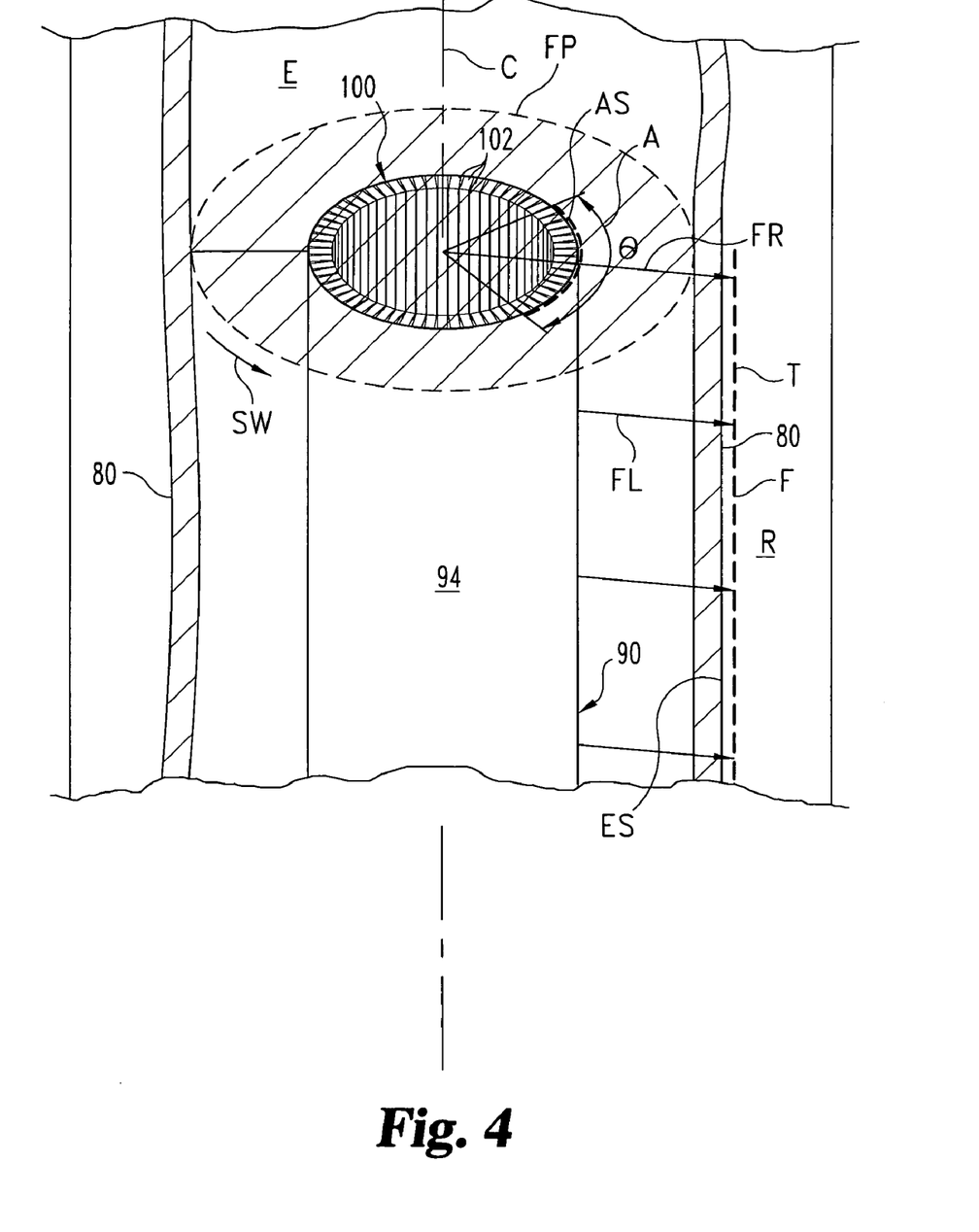
FIG. 4 is a schematic view of the ablation array of FIGS. 2 and 3 to illustrate certain operational aspects.

Referring additional to FIG. 4, array 100 of transducer device 90 is schematically shown to illustrate the spatial relationship of elements 102 with respect to tissue T of esophagus E. In the embodiment shown in FIG. 4, the longitudinal length of each elongate element 102 is greater than its width.

In one mode of ablation operation, different subsets of elements 102 are activated in a selected sequence in accordance with operating logic of subsystem 40. In one preferred embodiment, sixty-four (64) consecutive elements 102 are activated at one time corresponding to a 90 degree or less angular aperture A as shown in FIG. 4. The activation stimulus for each element 102 of a given subset is a sinusoidal electrical signal received from corresponding contacts 104 via cabling 68. By controlling relative phase and magnitude of the oscillatory electrical stimulus to each of the activated elements, a relatively narrowly focused region of ultrasonic acoustic power can be concentrated on region R of esophagus E. In FIG. 4, this focal region F is represented by a like-labeled broken line segment with focal length FL along focal axis FR represented by a radial ray. It should be appreciated that the focal point is located below the surface ES of the esophagus wall. In one implementation, different subsets of elements 102 are sequentially activated to advance focal region F along focal perimeter FP shown in FIG. 4. This sweep can continue for 360° to form ring-shaped ablation legion in the circumferentially surrounding tissue of esophagus E. Alternatively, the sweep can be less than 360° corresponding to a curved segment of ablated tissue, and/or the elements can be activated to form ablated segments spaced apart from one another along perimeter FP.

In one particular form, elements 102 are activated in element subsets each corresponding to an arc segment AS along the circumference of the array 100. Accordingly, activated elements 102 of a subset are consecutively positioned with each being immediately next to at least one other activated subset element 102 and with no unactivated elements 102 positioned between activated elements 102 in the subset segment AS. As element 102 is activated at one end of segment AS, element 102 at the other end of segment is deactivated, providing a new, overlapping subset of active elements 102 that includes 15 elements 102 of the prior subset. In this manner, the subsets change in sequence one element at a time at uniform time intervals until a circumferential lesion is formed. The rotational progression of focused ultrasonic energy about center axis C is represented by the counterclockwise direction of rotation shown with sweep arrow SW.

Figure 5:
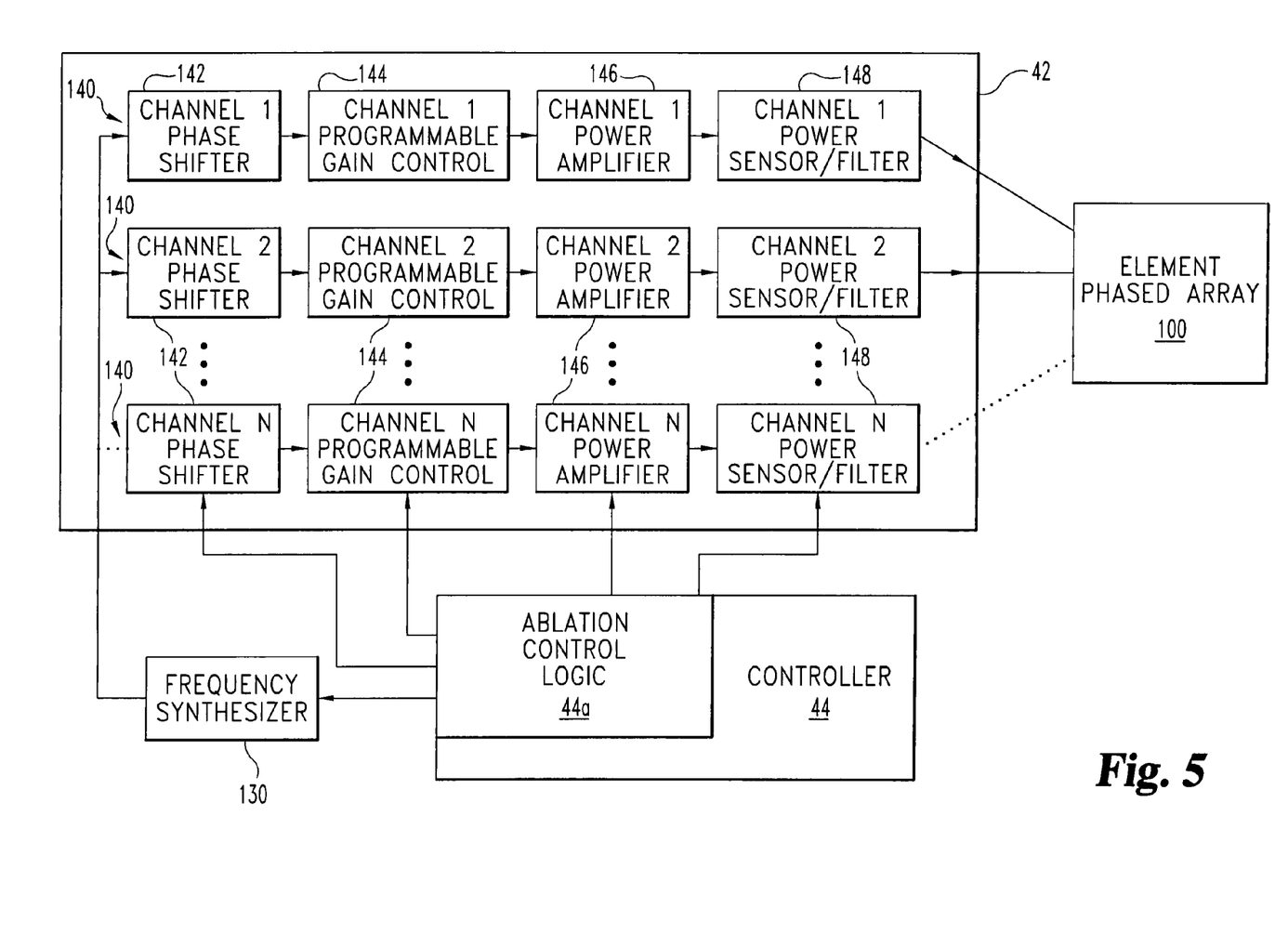
FIG. 5 is a schematic view of circuitry relating to operation of the transducer device of FIGS. 1-4 in one mode.

Referring additionally to FIG. 5, the circuitry and logic for operation of the array 100 in one form of tissue ablation mode in which different subsets of elements 102 are activated is shown. FIG. 5 illustrates analog circuitry 42 and the ablation control logic portion 44a of signal controller 44 associated with this mode in greater detail than shown in FIG. 1. This circuitry includes frequency synthesizer 130 that is controlled by ablation control logic 44a. Analog interface circuitry 42 includes a number N of independently controlled channels 140, that are each coupled to one corresponding element 102 of array 100. It should be appreciated that independently controlled channels 140 can be coupled to more than one corresponding elements 102 by using multiplexers to switch between different elements 102. While ablation control logic 44a is only shown connected to channel N, it should be understood that logic 44a is coupled to each channel 1-(N−1) in a like manner with ellipses representing any channels between channel 2 and channel N.

For the sweeping subset embodiment previously described, logic 44a of controller 44 is arranged to control the relative phase shift of the oscillating activation signal array the channels via independently controlled channel phase shifters 142 of circuitry 42. This phase shift stage includes a number of active, all-pass filters adjusted to provide different phase outputs in relation to one another, where the number of outputs desired corresponds to the number of differently phased elements 102 in an activated subset. The phase-shifted signals are provided to programmable gain controlled preamplifiers 144 in each channel 140 in a subsequent preamplification stage to account for any gain/loss changes that may have occurred during the all-pass filtering in the phase shift stage. The outputs of preamplifiers 144 are provided to high-frequency power amplifiers 146 in a subsequent amplification stage to amplify the signals by a fixed amount of gain for each channel 140. The final output gain can be controlled with the function generator and/or preamplifiers. The power amplifiers 146 are coupled to power sensors/filters 148 in each channel 140 which are then coupled to array 100. Power subsystem 36 provides a source of power adequate to provide a maximum power level of up to several watts per element 102 operating in the ablation mode. To provide for sequential activation of different subsets, the outputs of the amplifiers can be coupled to different elements 102 by way of one or more Digital Signal Processor (DSP)-controlled switching matrices or trees included in circuitry 42 (not shown).

In other embodiments, circuitry 42 can be differently configured for ablation mode operation, including arrangements to select between different subset quantities, relative phase relationships, amplification, and the like. In alternative forms, the activation pattern can sweep clockwise and/or include a different number of subset elements. In still other embodiments, the subset element quantity may vary from one subset to the next, subsets may be sequenced in a pattern that lacks a rotational progression, subsets may be constituted of nonconsecutive elements 102 (such that one or more elements are skipped or activated out of consecutive order), more than one element 102 may be activated or deactivated at the same time, a change from one activated subset to another activated subset may not include any of the same elements 102, and/or elements 102 may be active only one at a time. Additionally or alternatively, system 20 can be used to provide ablation treatment for other medical conditions and/or other types of tissue. For any of these variations, processing subsystem 40 can be correspondingly configured.

Figure 6:
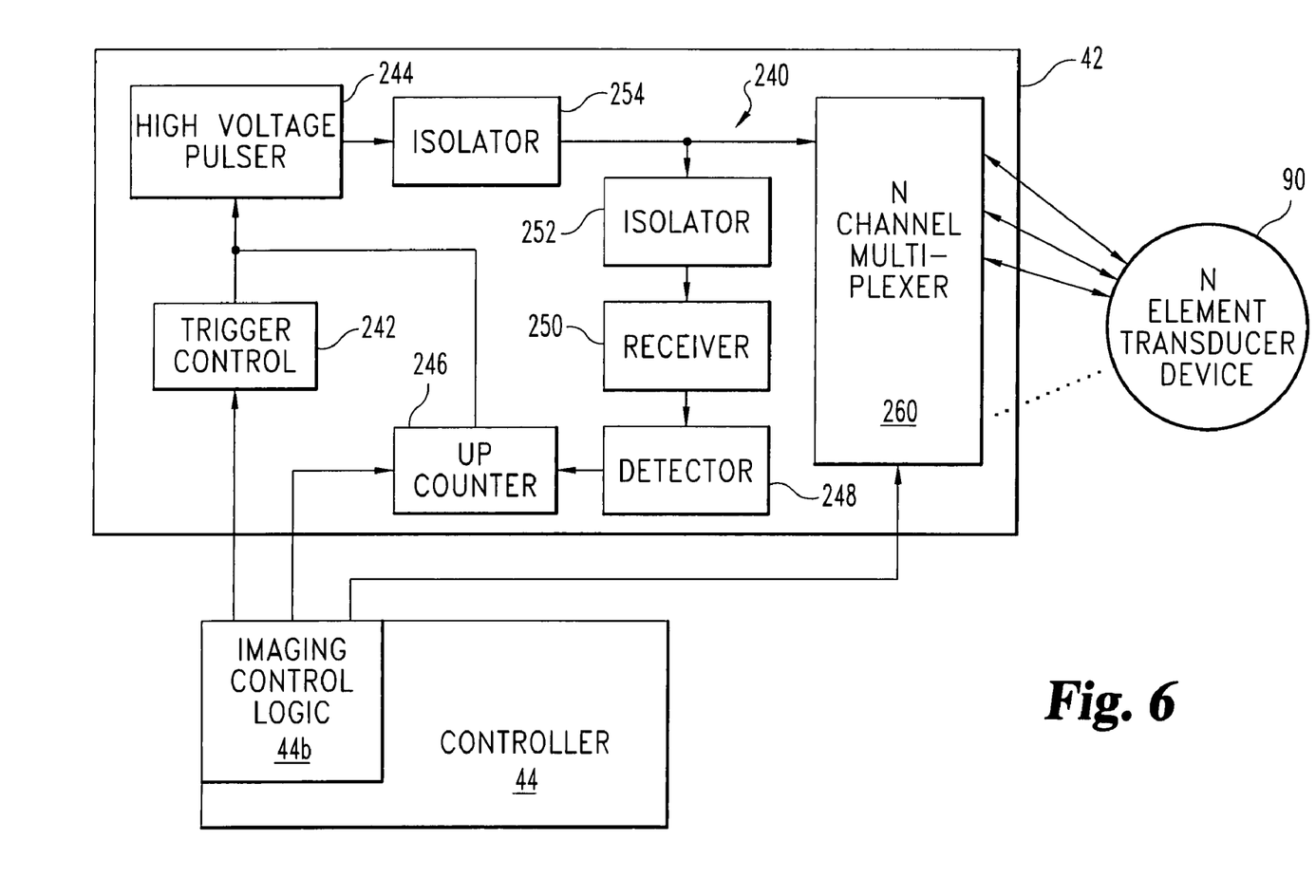
FIG. 6 is a schematic view of circuitry relating to operation of the transducer device of FIGS. 1-4 in another mode.

FIG. 6 illustrates aspects of processing subsystem 40 utilized for operation of the transducer device 90 in the location determination mode (A-mode) in greater detail. In this mode, one or more of elements 102 are utilized to sense position of distal end portion 70 relative to internal body region R and tissue T of esophagus E. As such, the location/imaging mode is used to guide the distal end portion, and in particular transducer 90 to a desired site. Accordingly, this guidance mode is used before ablation of tissue commences. In FIG. 6, portions of logic 44 and circuitry 42 are symbolically shown that are used for this location mode of operation. It should be appreciated that the circuitry/logic of this alternative A-mode of operation could be provided with one or more dedicated components completely separate from circuitry/logic for ablation. Alternatively, both modes can be tightly integrated in a single unit or multiple units/components. In all cases, logic 44 and circuitry 42 are provided to broadly illustrative functionality that can be embodied in any of a number of ways from a single unit to multiple units/components/devices that are remotely located relative to each other. In the illustrated embodiment of FIG. 6, control logic portion 44b of controller 44 provides operating logic for the location mode, and is correspondingly operatively coupled to parts of analog circuitry 42 utilized for such mode. Circuitry 42 includes trigger control 242, up-counter 246, high voltage pulser 244, isolator 254, isolator 252, receiver 250, detector 248, and multiplexer 260. Multiplexer 260 is connected to transducer device 90.

Figure 7:
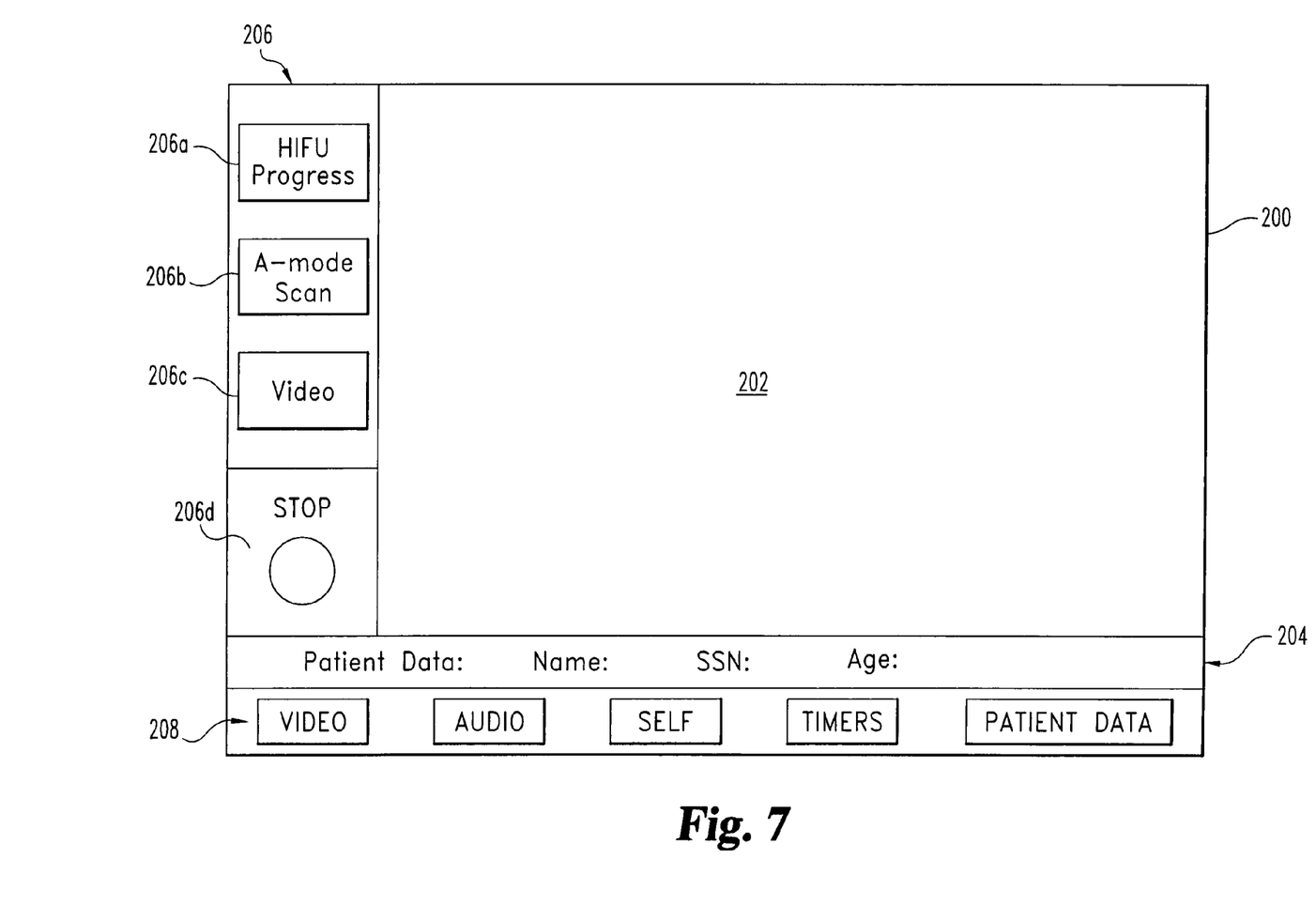
FIG. 7 is a diagrammatic view of an operator control display for the system of FIG. 1.

Referring to FIG. 7, an operator control display 200 is illustrated. Display 200 enables the operator to control the device in its tissue ablation mode and location determination mode. Display 200 can be implemented in accordance with operating logic of processor 46 and output via device 34. The display 200 includes an image of the body 202, patient data fields 204, software control buttons 206 and data tabs 208. The patient data fields 204 can include patient data, name, social security number, and age just to name a few possibilities. It should be appreciated however, that other appropriate fields can be included as desired. Software control buttons 206 include high intensity focused ultrasound (HIFU) progress monitoring button 206a, location determination scan button 206b, video select button 206c, and a stop button 206d. When selected, button 206a activates ablation mode and shows a visual representation corresponding to ablation progress; and button 206b depicts a scan representing the location/position of transducer 90. Video select button 206c selects video through the camera and stop button 206A halts the current operation—such as ablation. The data tabs 208 include video settings, audio settings, system self-check, timers, and patient information. It should be appreciated that the data tabs 208 can be in the form of a menu bar and all of the menus can contain further options related to the implementation of the device. It is understood that the data tabs can include more and different tabs if so desired. The display 200 is generally configured with the image 202 in the upper right corner, the software control buttons 206 as a column down the left side of the display 200, the patient data fields 204 as the second row from the bottom, and the data tabs 208 as the bottom row on the display 200. However, it should be appreciated that other configurations of the display 200 can be utilized as would occur to those skilled in the art. Image 202 provides a visual representation of array 100 relative to the surrounding tissue T of esophagus E. In one form, some or all of image 202 is a window that shows an image of distal end portion 70 during use with or without overlays corresponding to focal information and active elements. Further, operator equipment 30 can include limits on its operation to prevent improper use and/or can monitor one or more physiological aspects of the patient to accordingly adjust operation with or without operator intervention.

Figure 8:
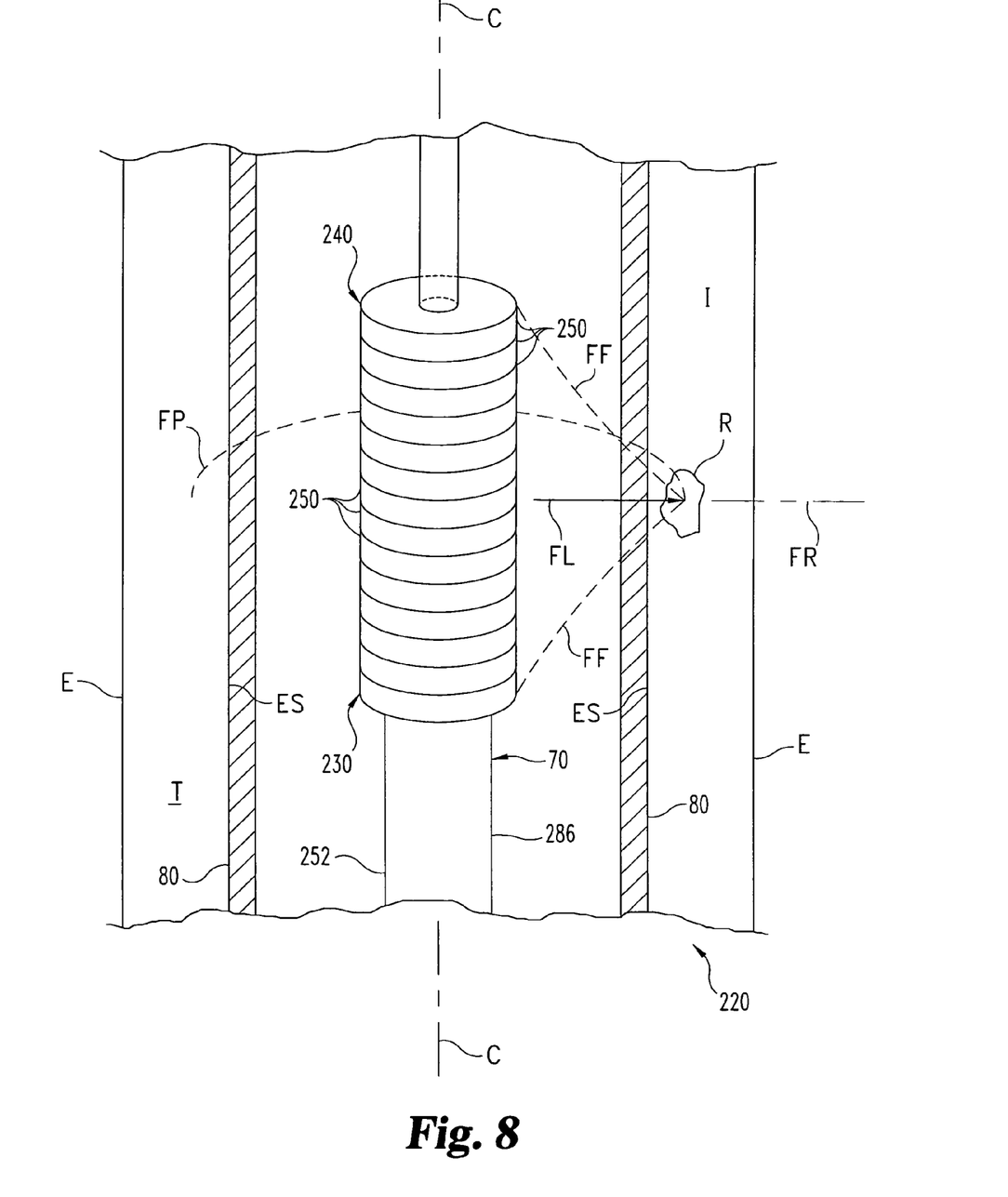
FIG. 8 is a partial, schematic view of a second type of transducer device.

An alternative transducer device arrangement is illustrated in the partial view of FIG. 8 as system 220; where like reference numerals refer to like features previously described. System 220 includes transducer device 230 surrounded by balloon 80. Transducer device 230 is sized and shaped relative to balloon 80 the same as transducer device 90 of system 20. Transducer device 230 includes support member 286 that carries ablation array 240 of transducer device 230. Member 286 and ablation array 240 are shaped generally in the form of a right circular cylinder about centerline axis C. Ablation array 240 includes a number of piezoelectric elements 250 each in the shape of a generally circular ring or toroid. Elements 250 generate acoustic energy in the same general manner as previously described in conjunction with the operation of elements 102, except that the shape of each element 250 radiates acoustic energy in a generally circular pattern about a corresponding portion of axis C. Elements 250 are each generally rigid, and sized and shaped the same, and are evenly spaced apart from one another, being equidistant from axis C. Member 286 includes a backing rod core, and optionally one or more concentric acoustic layers that can be arranged as described for transducer 90, or as would otherwise be desired.

In FIG. 8, center axis C is generally parallel to the view plane. In a preferred embodiment of the present application, elements 250 number at least 8. In a more preferred embodiment, elements 250 number at least 64. The illustrated portion of system 220 corresponds to distal end portion 70 of an endoscope 252 of an endoscopic subsystem that can be utilized in the same manner as described in connection with system 20, and operated with the same operator equipment 30 external to a patient when in use.

In one mode of ablation operation, elements 250 are activated in different relative phases in accordance with operating logic to focus ultrasonic ablation energy on region R of tissue T of esophagus E. During this manner of operation, a relatively narrowly focused region of ultrasonic acoustic power can be concentrated on region R from different elements 250 along axis C in correspondence to focus lines FF. The focal length FL along focal axis FR is represented by a radial ray from transducer device 230 that originates at axis C. It should be appreciated that the focal point is located below the surface ES of the esophagus wall. Because of the shape of elements 250, the ultrasonic ablation energy is simultaneously focused in tissue T along a circumferential ring about axis C, which is designated focal perimeter FP in FIG. 8. The position of focal perimeter FP can be moved longitudinally along axis C (up and down in the FIG. 8. orientation), to ablate different circumferential regions by controlling the relative phase/magnitude of energy used to activate elements 250.

Figure 9:
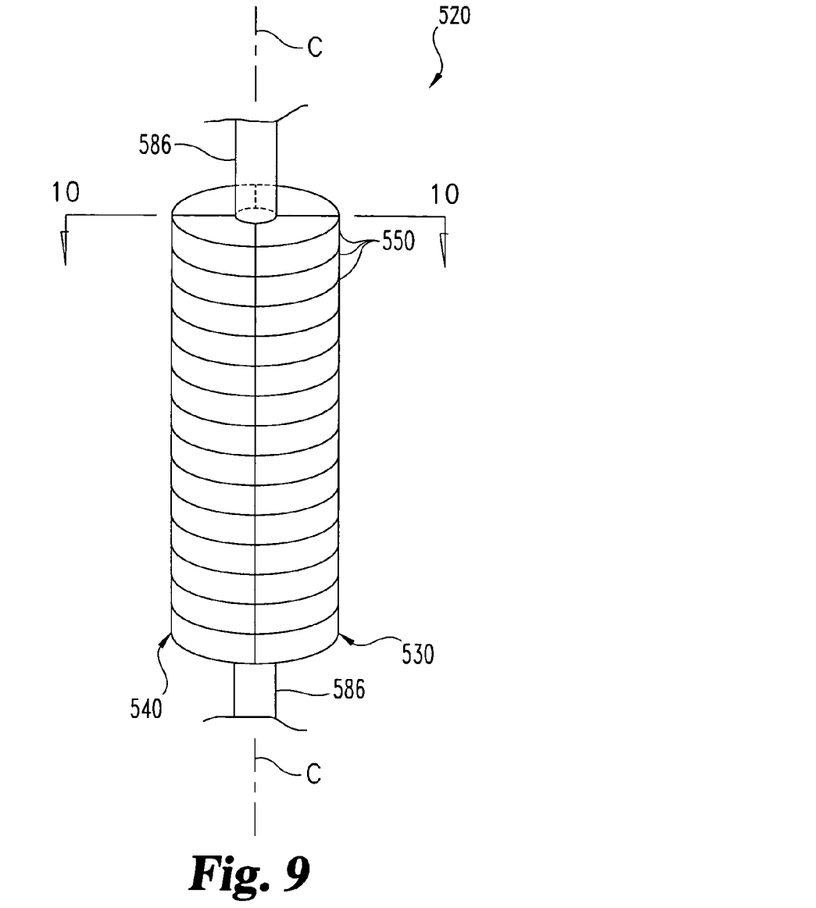
FIG. 9 is a partial, schematic view of a third type of transducer device.
Figure 10:
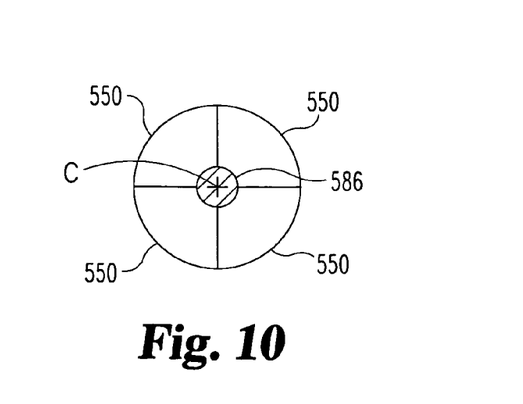
FIG. 10 is a partial, schematic view of the third transducer device taken along section line 10-10 of FIG. 9.

Still another transducer device arrangement is illustrated in FIGS. 9 and 10 as system 520; where like reference numerals refer to like features previously described. System 520 includes transducer device 530. Transducer device 530 may be used within a balloon and sized and shaped appropriately relative to such balloon on the distal end portion of an endoscopic subsystem for esophageal treatment in the manner previously described in connection with systems 20 and 220. Furthermore, the same operator equipment can be adapted for use with system 520 as described hereinafter. Transducer device 530 includes support member 586 that has a support core and any desired acoustic layers configured in a manner previously described. Member 586 carries ablation array 540 that is generally shaped in the form of a right circular cylinder about centerline axis C. Ablation array 540 includes a number of piezoelectric elements 550 each in the shape of a segment of a generally circular ring or toroid. As illustrated, each element 550 subtends an angle of about 90 degrees with respect to a sector of a circle with an origin coincident with centerline axis C. Centerline axis C is parallel to the view plane of FIG. 9 and is perpendicular to the view plane of FIG. 10 and, therefore, is represented by crosshairs in FIG. 10. Elements 550 generate acoustic energy in generally the same manner as previously described in conjunction with operation of elements 102 and 250, except that the shape of each element radiates acoustic energy in correspondence to a sector of a circle. Specifically, for the segment shapes shown in FIGS. 9 and 10, acoustic energy radiates from axis C in an angular range of 90 degrees for each elements 550. Elements 550 are each generally rigid, and sized and shaped the same, and are evenly spaced apart from one another, being equidistant from axis C. In a preferred embodiment, elements 550 number at least 32. In a more preferred embodiment, elements 550 number at least 128.

In one mode of ablation operation, elements 550 are activated in different subsets and/or in different relative phases to one another in accordance with operating logic of the external operator equipment, such as a processing subsystem. During this manner of operation, a relatively narrowly focused region of ultrasonic acoustic power can be concentrated on a region R of tissue which is limited to its 90 degree pattern of radiation, in contrast to the fully circumferential pattern provided by system 220, and the generally linear pattern provided by system 20. In a manner analogous to system 20, the ablation energy pattern can be swept about axis C to define a partial or complete circumferential ablation region, limited only by the angular region defined by the corresponding shape of elements 550. In other words, segmented elements subtending smaller or greater angles would correspondingly provide different arcuate regions of ablation along the tissue. Correspondingly, in other embodiments, it is envisioned that different segment shapes could be utilized defining different radiation patterns. In one preferred embodiment, the corresponding sector occupied by an element segment is 90 degrees or less. In a more preferred embodiment, the sector occupied by a correspondingly shaped element segment is 45 degrees or less. Such arcuate ring-shaped segments can be used in other transducers in combination with the circular rings of system 220, and/or with segments of different shapes and corresponding ultrasonic energy radiation patterns. In still another embodiment, one segment is stacked on another such that the segments do not each end at a line approximately parallel to axis C, but rather are offset to form a "stair-step" pattern that approximately follows a helical path about axis C.

Figure 11:
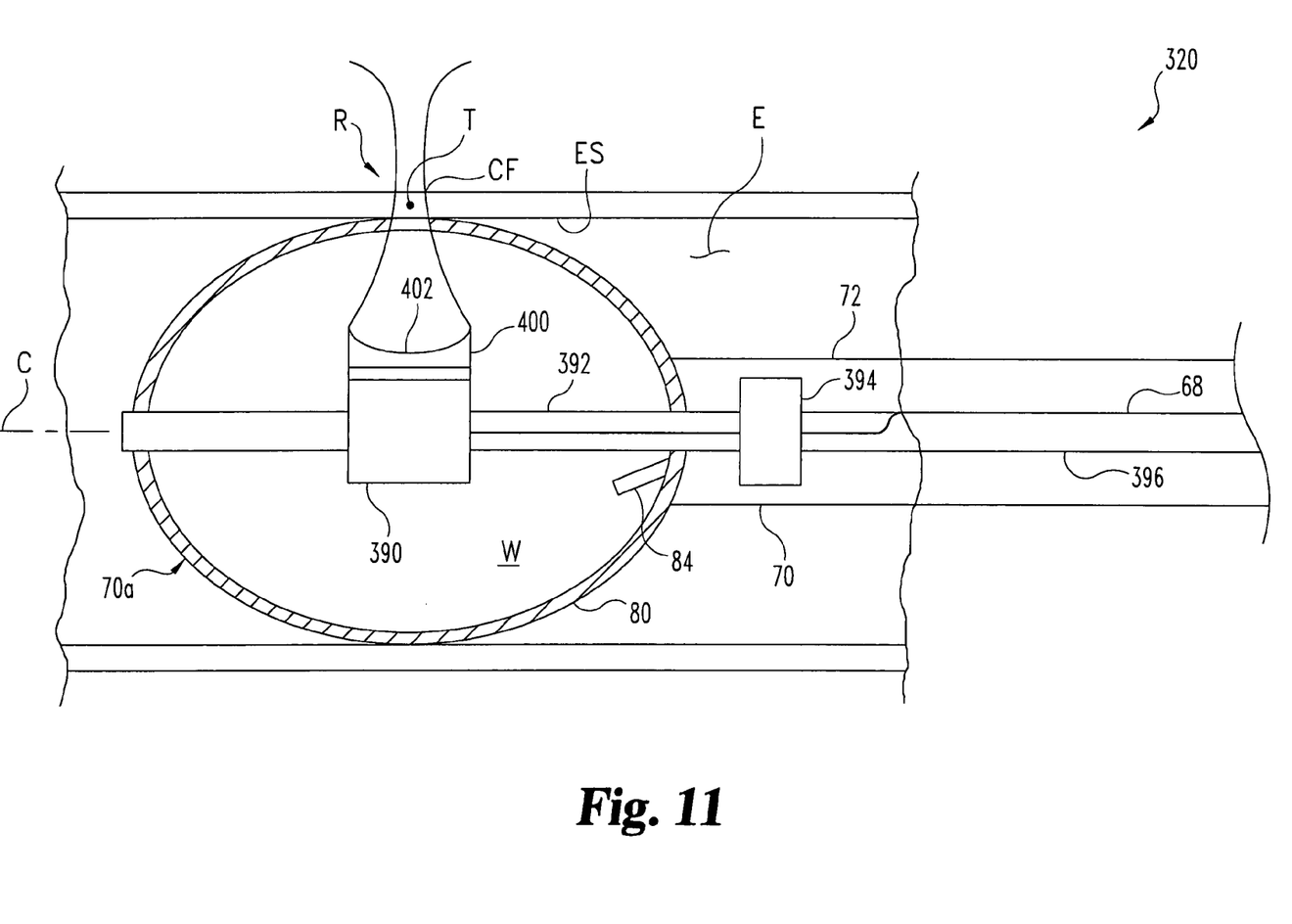
FIG. 11 is a partial, schematic view of a fourth type of transducer device.

Another alternative transducer device arrangement is illustrated in FIG. 11 as system 320; where like reference numerals refer to like features previously described. System 320 includes distal end portion 70*a* which houses transducer device 390. Rotating connector rod 392 carries transducer device 390 and is coupled to motor 394. Motor 394 is located outside balloon 80 on elongate flexible body 72 to selectively rotate connector rod 392 along with transducer device 390 about axis C. Transducer device 390 is fixed to rod 392. Transducer control cable 68 and central pathway 396 are located within elongate flexible body 72 connecting proximal end portion 60 (not shown) and distal end portion 70*a*. In this embodiment, transducer device 390 includes one piezoelectric element 400 with a concave face 402. The alternative system 320 operates in the same manner as system 20 except transducer device 390 has a single piezoelectric element 400 rather than multiple elements 102. The concave face 402 of piezoelectric element 400 creates focus lines CF to focus onto a specific narrow tissue area T on esophagus E below surface ES. This arrangement allows for subsystem 40 activation to direct tissue ablation in a small region. Further, the motor 394 exerts a force utilized to rotate connecting rod 392 which in turn rotates transducer device 390. This allows for tissue ablation to occur in the entire circumference of tissue T at a specific location of esophagus E if so desired.

System 320 also includes operator equipment (not shown) similar to operator equipment 30 discussed with the other embodiments. The operator equipment connected with system 320 would be adapted for activation of the single piezoelectric element 400. Also similar to the other embodiments, system 320 can be operated in a mode to determine the location of transducer device 390 relative to region R. It should be appreciated that in other embodiments, more than one piezoelectric element of the same or different types could be included. In one particular form, face 402 is of a spherically concave type. In other forms, face 402 has a different type of concavity or is not concave at all, resulting in a different focal pattern (if any).

Generally referring to FIGS. 1-11, the embodiments of system 20, 220, and 320 can be completely or partially combined in other embodiments. For embodiments with more than one ultrasonic element, such elements may be the same or different from one another. Moreover, other embodiments may operate with only an ablation or location determination mode, but not both. Furthermore, the operator interfacing, circuitry, software, and the like can vary to accomplish the desired purposes as would occur to those skilled in the art.

All publications, patents, and patent applications cited in this specification are herein incorporated by reference as if each individual publication, patent, or patent application were specifically and individually indicated to be incorporated by reference and set forth in its entirety herein. Any theory, mechanism of operation, proof, or finding stated herein is meant to further enhance understanding of the present invention and is not intended to make the present invention in any way dependent upon such theory, mechanism of operation, proof, or finding. While the invention has been illustrated and described in detail in the drawings and foregoing description, the same is to be considered as illustrative and not restrictive in character, it being understood that only the selected embodiments have been shown and described and that all changes, modifications, and equivalents of the inventions as defined herein or by the following claims are desired to be protected.

What is claimed is:

1. A medical treatment device, comprising:
    a distal end portion opposite a proximal end portion, the proximal end portion being operable to connect to operator equipment outside a patient's body, the distal end portion having a longitudinal axis and being operable to extend through a passageway of a patient's body to an internal body region;
    a balloon located at the distal end portion;
    a conduit in fluid communication with the balloon, the conduit extending from a balloon control port at the proximal end portion to the balloon;
    a view port at the distal end portion to visualize the internal body region, the view port being operatively coupled to an image communication pathway extending between the distal end portion and the proximal end portion; and
    an acoustic ablation array positioned inside the balloon, the array including several piezo electric elements positioned about the longitudinal axis of the distal end portion;
    wherein the elements are each elongate with a longitude generally parallel to said longitudinal axis, with the length of each elongate element being greater than its width;
    the array being operatively coupled to control cabling, the control cabling extending between the distal end portion and the proximal end portion and being effective to carry control signals to activate one or more of the elements in a different manner than one or more other of the elements to correspondingly focus acoustic energy relative to the internal body region.

2. The device of claim 1, wherein the elements number at least 256.

3. The device of claim 1, wherein the image communication pathway includes an optic fiber, the distal end portion includes a video camera, and the view port is provided with the video camera.

4. The device of claim 1, wherein the acoustic ablation array includes a flexible substrate carrying the elements, the substrate being positioned between the elements and the balloon and, further comprising a number of electrically conductive contacts carried with the substrate, the contacts each being electrically coupled to a corresponding one of the elements and being positioned between the substrate and the corresponding one of the elements; and
    further comprising a backing rod, the substrate being positioned about the backing rod with the elements each being positioned between the backing rod and the substrate.

5. The device of claim 1, further comprising means for providing a phase difference between the one or more elements and the one or more other elements to provide the different manner of activation.

6. The device of claim 1, further comprising:
    means for controlling the balloon to selectively hold the balloon in a desired position along the passageway, said controlling means being coupled to the control port to selectively provide liquid under pressure through the conduit to an interior of the balloon to expand the balloon and to selectively extract the liquid from the balloon through the conduit to collapse the balloon; and
    means for displaying one or more images of the internal body region to an operator, said displaying means being coupled to the image communication pathway; means for activating one or more of the elements in an imaging operation mode to determine position of the array relative to the internal body region; and
    means for ablating tissue by activating different subsets of the elements in an ablation mode of operation to controllably focus acoustic energy on the internal body region and correspondingly ablate tissue therealong.

7. An endoscope, comprising:
    a proximal end portion opposite a distal end portion;
    said distal end portion having a longitudinal axis and being operable to extend through a passageway of a patient's body to an internal body region;
    means for positioning the distal end portion proximate to an internal body region through a passageway of a patient's body;
    means for viewing the internal body region through a view port at the distal end portion when positioned proximate to the internal body region;
    means for imaging the internal body region with one or more piezoelectric elements positioned at the distal end portion;
    means for ablating tissue of the internal body region with the one or more piezoelectric elements; and
    means for selectively holding the distal end portion in position in the passageway proximate to the internal body region, the holding means including a balloon positioned about the one or more piezoelectric elements;
    wherein said means for ablating tissue comprises an array of piezoelectric elements positioned about the longitudinal axis of the distal end portion; and wherein the elements are each elongate with a longitude generally parallel to said longitudinal axis, with the length of each elongate element being greater than its width.

* * * * *

UNITED STATES PATENT AND TRADEMARK OFFICE
CERTIFICATE OF CORRECTION

PATENT NO.       : 7,628,785 B2                                             Page 1 of 1
APPLICATION NO.  : 10/868415
DATED            : December 8, 2009
INVENTOR(S)      : Hadjicostis et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1478 days.

Signed and Sealed this

Twenty-first Day of December, 2010

David J. Kappos
*Director of the United States Patent and Trademark Office*